US008818480B2

(12) United States Patent
Okuda et al.

(10) Patent No.: US 8,818,480 B2
(45) Date of Patent: Aug. 26, 2014

(54) BIOLOGICAL INFORMATION DETECTION DEVICE

(71) Applicant: Seiko Instruments Inc., Chiba (JP)

(72) Inventors: Hideki Okuda, Chiba (JP); Teruo Kato, Chiba (JP); Dai Terasawa, Chiba (JP); Takahiro Kaneko, Chiba (JP); Hiroshi Kawamata, Chiba (JP); Nobukazu Omori, Chiba (JP); Hideaki Koshoji, Chiba (JP)

(73) Assignee: Seiko Instruments Inc. (JP)

( * ) Notice: Subject to any disclaimer, the term of this patent is extended or adjusted under 35 U.S.C. 154(b) by 21 days.

(21) Appl. No.: 13/669,847

(22) Filed: Nov. 6, 2012

(65) Prior Publication Data

US 2013/0137956 A1 May 30, 2013

(30) Foreign Application Priority Data

Nov. 8, 2011 (JP) .................................. 2011-244574

(51) Int. Cl.
*A61B 5/0402* (2006.01)
*A61B 5/0408* (2006.01)

(52) U.S. Cl.
USPC .......................................... 600/390; 600/509

(58) Field of Classification Search
CPC ............. A61B 5/04085; A61B 5/6823; A61B 5/6831; A61B 2562/182; A61B 2562/227
USPC ................................................ 600/390, 509
See application file for complete search history.

(56) References Cited

U.S. PATENT DOCUMENTS

| | | | | |
|---|---|---|---|---|
| 4,809,700 A * | 3/1989 | Castelli | ......................... | 600/384 |
| 4,889,131 A * | 12/1989 | Salem et al. | .................. | 600/484 |
| 5,491,474 A * | 2/1996 | Suni et al. | ................ | 340/870.31 |
| 5,778,880 A * | 7/1998 | Chen | ............................. | 600/509 |
| 6,272,365 B1 * | 8/2001 | Ronkainen et al. | ........... | 600/390 |
| 6,553,247 B1 * | 4/2003 | Rytky | ............................ | 600/386 |
| 6,600,942 B2 * | 7/2003 | Nissila et al. | ................ | 600/372 |
| 7,039,456 B2 * | 5/2006 | Chen | ............................. | 600/509 |
| 7,167,737 B2 * | 1/2007 | Fujii et al. | ..................... | 600/390 |
| D603,521 S | 11/2009 | Lindberg et al. | ............. | D24/187 |
| 8,060,191 B2 * | 11/2011 | Chen | ............................. | 600/509 |
| 2005/0096556 A1 | 5/2005 | Chen | ............................. | 600/509 |
| 2006/0058695 A1 * | 3/2006 | Chen | ............................. | 600/509 |
| 2007/0093707 A1 * | 4/2007 | Noguchi | ........................ | 600/390 |
| 2009/0099472 A1 * | 4/2009 | Remmert et al. | ............. | 600/534 |
| 2010/0191090 A1 * | 7/2010 | Shin et al. | ..................... | 600/388 |

FOREIGN PATENT DOCUMENTS

JP      3095486         7/2003

OTHER PUBLICATIONS

Patent Abstracts of Japan, Publication No. 2004-121360, Publication Date Apr. 22, 2004.

* cited by examiner

*Primary Examiner* — Lee S Cohen
(74) *Attorney, Agent, or Firm* — Adams & Wilks

(57) ABSTRACT

A biological information detection device includes a main body portion, a heartbeat detection portion, formed integrally with the main body portion, which has electrodes that come into contact with a biological surface, and a fixing band, detachably provided to the main body portion, which mounts the main body portion and the heartbeat detection portion to a user. A sealing portion for securing sealing of an electrical connection portion is provided in the periphery of the electrical connection portion that electrically connects the main body portion to the electrodes of the heartbeat detection portion.

20 Claims, 12 Drawing Sheets

BIOLOGICAL INFORMATION DETECTION DEVICE

BACKGROUND OF THE INVENTION

1. Field of the Invention

The present invention relates to a biological information detection device that detects a biological signal by installing an electrode on the biological surface of the human body.

2. Background Art

Among these kinds of biological information detection devices, there is, for example, a device that detects an electro-cardiac signal generated in association with a heartbeat, and measures a heart rate from the biological surface. As such a biological information detection device, there is, for example, a device which includes a main body portion having a detection circuit board and the like built-in, and a strap which mounts the main body portion to the human body, the strap being provided with a pair of electrodes. The main body portion and the strap are provided with an electrical connection portion for electrically connecting a detection circuit board of the main body portion to an electrode of the strap.

Based on such a configuration, an electro-cardiac signal generated in association with a heartbeat is detected by bringing a pair of electrodes into contact with the chest (biological surface) of the human body, and the main body portion derives a heart rate on the basis of she detected electro-cardiac signal.

Further, among the biological information detection devices, there is, for example, a device in which the main body portion is detachably provided to the strap from the viewpoint of maintenance such as cleaning of the strap. When the main body portion is mounted to the strap, the electrical connection portion provided to the strap and the electrical connection portion provided to the main body portion are mechanically connected to each other, and the detection, circuit board and the electrode are electrically connected to each other (see, for example, Specification of U.S. Patent Application Publication No. 2005/0096556 and U.S. Design Registration No. 603,521).

SUMMARY OF THE INVENTION

However, in the above-mentioned related, art, in order to detachably form the electrical connection portion provided to the strap and the electrical connection portion provided to the main body portion to each other, it is necessary to expose these electrical connection portions to the outside. For this reason, there is concern of the electrical connection portions being corroded or foreign substances infiltrating into the electrical connection portions due to exposure of each of the electrical connection portions to the external environment such as sweat, which leads to an occurrence of defective detection. In addition to this, there is concern of the electrode portion being exposed to a cleaning solution in association with cleaning of the strap at the time of maintenance, and thus the electrical parts such as the electrode and the electrical connection portion being damaged.

Consequently, the present invention is contrived in view of such circumstances, and an object thereof is to provide a biological information detection device capable of preventing defective detection from occurring while securing good maintenance.

According to an aspect of the present invention, there is provided a biological information detection device including: a device main body: a biological signal detection portion, formed integrally with the device main body, which has an electrode that comes into contact with a biological surface; and a fixing portion, detachably provided to the device main body, which mounts the device main body and the biological signal detection portion to a human body, wherein a sealing portion for securing sealing of an electrical connection portion is provided in the periphery of the electrical connection portion that electrically connects the device main body to the electrode of the biological signal detection portion.

According to such a configuration, it is possible to prevent the electrical connection portion from being exposed to the outside while detachably forming the heart rate meter main body and the fixing portion to each other. For this reason, it is possible to prevent defective detection of the heartbeat measurement device from occurring while securing good maintenance.

In addition, the biological signal detection portion is integrally provided in the device main body, and the fixing portion is detachably provided to the device main body, thereby allowing the biological signal detection portion to be separated from the fixing portion. For this reason, for example, in cleaning at time of maintenance, it is possible to perform cleaning of a simple fixing portion, and to reliably prevent defects from occurring in electrical parts such as the electrode and the electrical connection portion.

In the biological information detection device according to the aspect, the sealing portion may be integrally formed in the biological signal detection portion.

According to such a configuration, it is possible to reduce the number of parts, and to improve ease of assembly and reduce costs.

In the biological information detection device according no the aspect, a groove may be formed between the electrical connection portion and the sealing portion.

According to such a configuration, it is possible to easily elastically deform the electrical connection portion, and to reduce contact resistance of the electrical connection portion to the device main body. As a result, it is possible to improve adhesion of the sealing portion to the device main body and the biological signal detection portion, and to improve sealing thereof.

In the biological information detection device according to the aspect, the biological signal detection portion may be formed from conductive elastomer, and the conductive elastomer may serve as the electrode.

According to such a configuration, it is possible to easily elastically deform the biological signal detection portion, and to increase adhesion of the electrode to the biological surface. For this reason, it is possible to detect the biological signal with a higher degree of accuracy.

In addition, the sealing portion is formed from conductive elastomer, thereby allowing adhesion of the sealing portion to be increased by elastic deformation of the sealing portion. For this reason, it is possible to more reliably increase sealing of the electrical connection portion.

According to the present invention, it is possible to prevent the electrical connection portion from being exposed to the outside while detachably forming the heart rate meter main body and the fixing portion to each other. For this reason, it is possible to prevent defective detection of the heartbeat measurement device from occurring while securing good maintenance.

In addition, the biological signal detection portion is integrally provided to the device main body, and the fixing portion is detachably provided to the device main body, thereby allowing the biological signal detection portion to be separated from the fixing portion. For this reason, for example, in cleaning at time of maintenance, it is possible to perform cleaning of a simple fixing portion, and to reliably prevent defects from occurring in electrical, parts such as the electrode and the electrical connection portion.

DETAILED DESCRIPTION OF THE INVENTION

First Embodiment

Heartbeat Measurement Device

Next, a first embodiment of the present invention will be described with reference to FIGS. 1 to 9.

Figure 1:
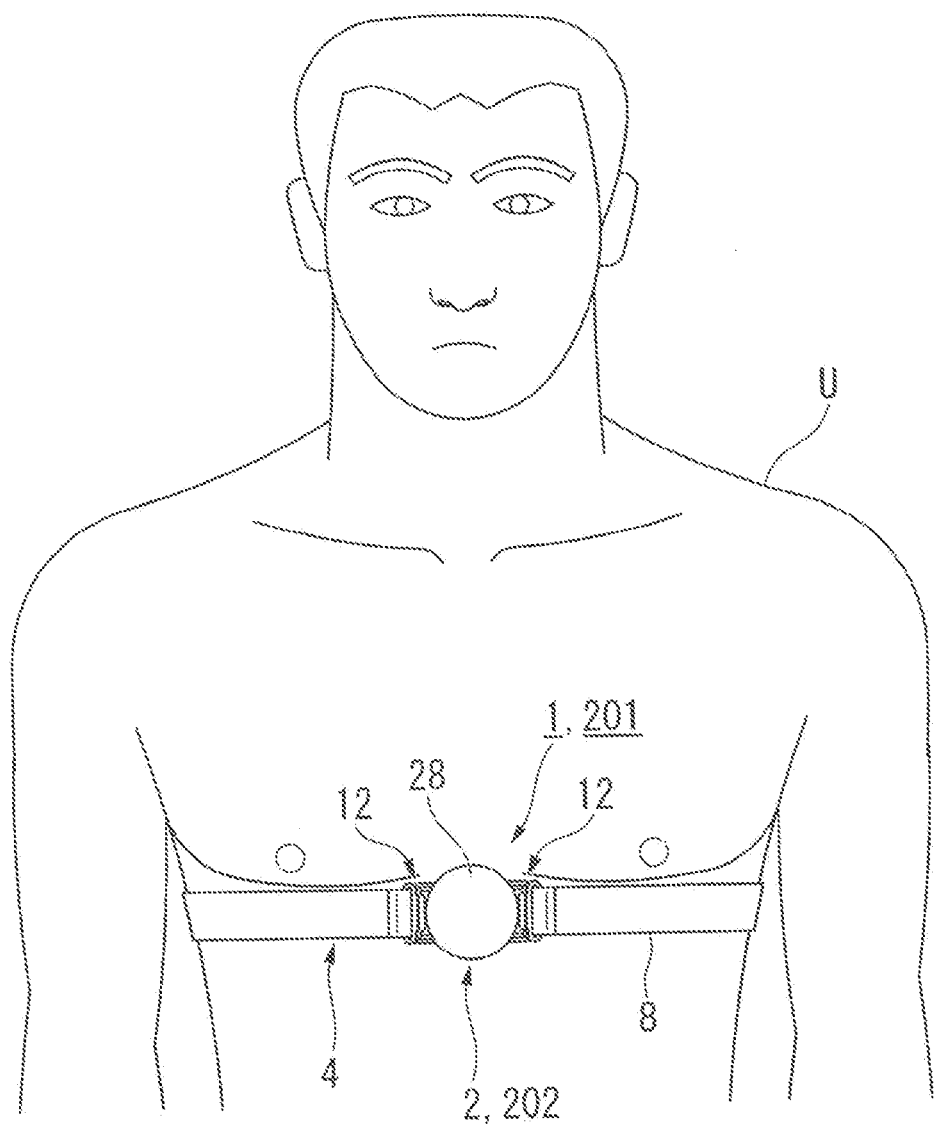
FIG. 1 is an explanatory diagram illustrating a state where a heartbeat measurement device according to a first embodiment of the present invention is installed on a user.
Figure 2:
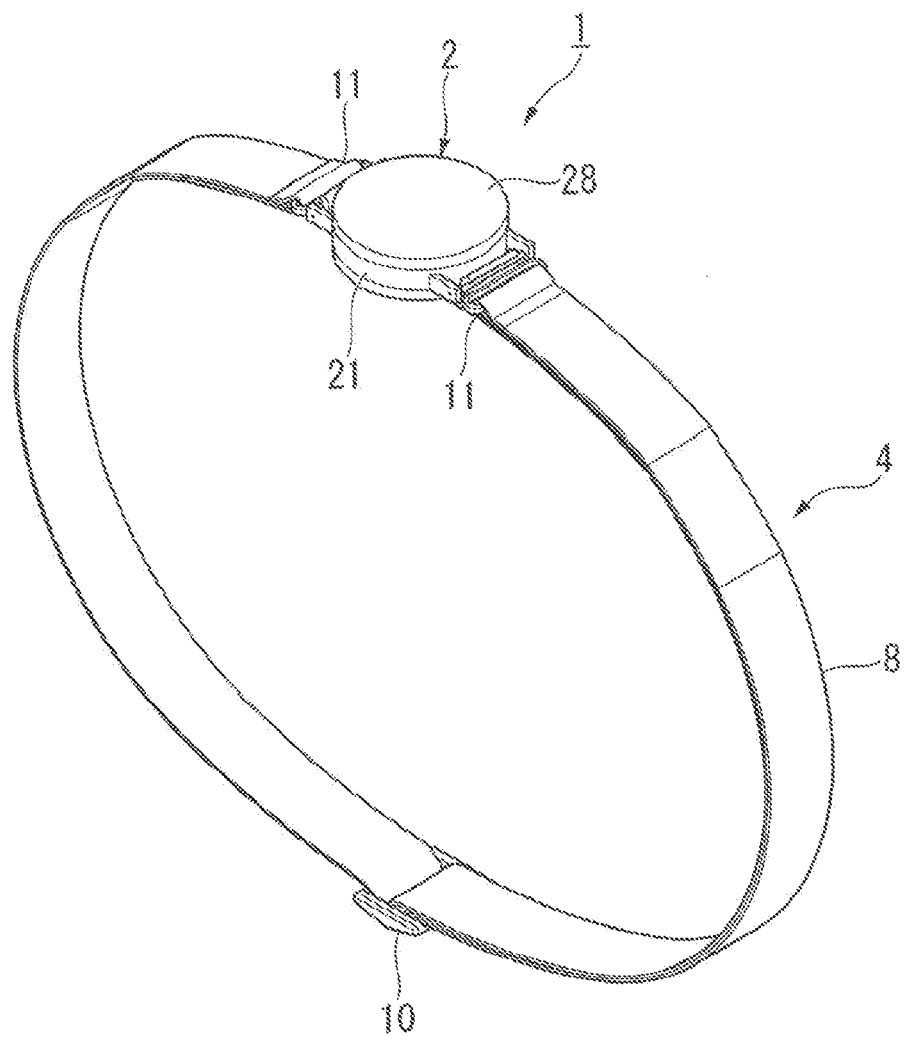
FIG. 2 is a perspective view illustrating the heartbeat measurement device according to the first embodiment of the present invention.
Figure 3:
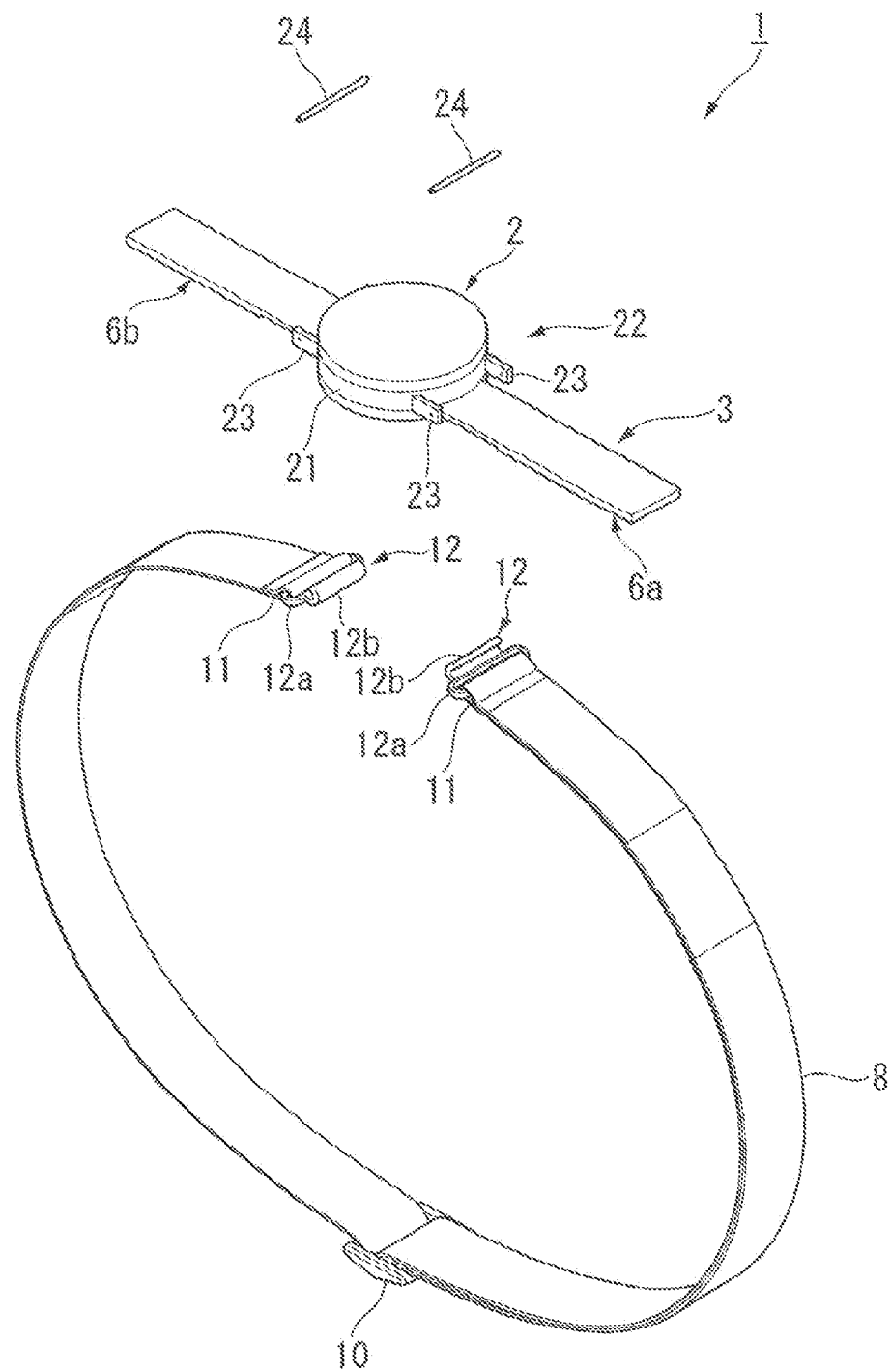
FIG. 3 is an exploded perspective view of a portion of the heartbeat measurement device according to the first embodiment of the present invention.

FIG. 1 is an explanatory diagram illustrating a state where a heartbeat measurement device 1 which is a biological information detection device according to the present invention is installed on a user U, FIG. 2 is a perspective view illustrating the heartbeat measurement device 1, and FIG. 3 is an exploded perspective view of a portion of the heartbeat measurement device 1.

Meanwhile, in the following description, the side which comes into contact with the user U in a state where the heartbeat measurement device 1 is mounted by the user U is expressed as the back side, and the surface on the side opposite to this back side and the side directed to the outside is expressed as the front side, and the like.

As shown in FIGS. 1 to 3, the heartbeat measurement device 1 is mounted to the chest which is a biological surface of the user U to detect an electro-cardiac signal generated in association with heartbeat, and wirelessly communicates the detected electro-cardiac signal. The heartbeat measurement device 1 includes a main body portion 2, a heartbeat detection portion 3 formed integrally with the main body portion 2, and a fixing band 4 which mounts the main body portion 2 and the heartbeat detection portion 1 to the chest of the user U.

The fixing band 4 is formed in a substantially ring shape so as to be mounted over the whole circumference of the chest of the user U. More specifically, the fixing band 1 includes a strap 8 having elasticity which is formed in a substantially belt shape. Meanwhile, the strap 8 may not only be elastic, bus also may be non-elastic.

A length adjustment member 10 for adjusting the length of the strap 8 is provided substantially at the center of the strap 8 in the long-side direction. In addition, ring portions 11 and 11 formed by folding back terminal portions of the strap 8 are respectively provided on both ends of the strap 8 in the long-side direction.

The two ring portions 11 and 11 are respectively provided with a strap attaching and detaching member 12. The strap attaching and detaching member 12 is constituted by a ring-shaped portion 12a inserted into the ring portions 11 and 11, and a hook portion 12b formed integrally with one side surface of the ring-shaped portion 12a. The hook portion 12b is engaged with the main body portion 2.

Main Body Portion and Heartbeat Detection Portion

Figure 4:
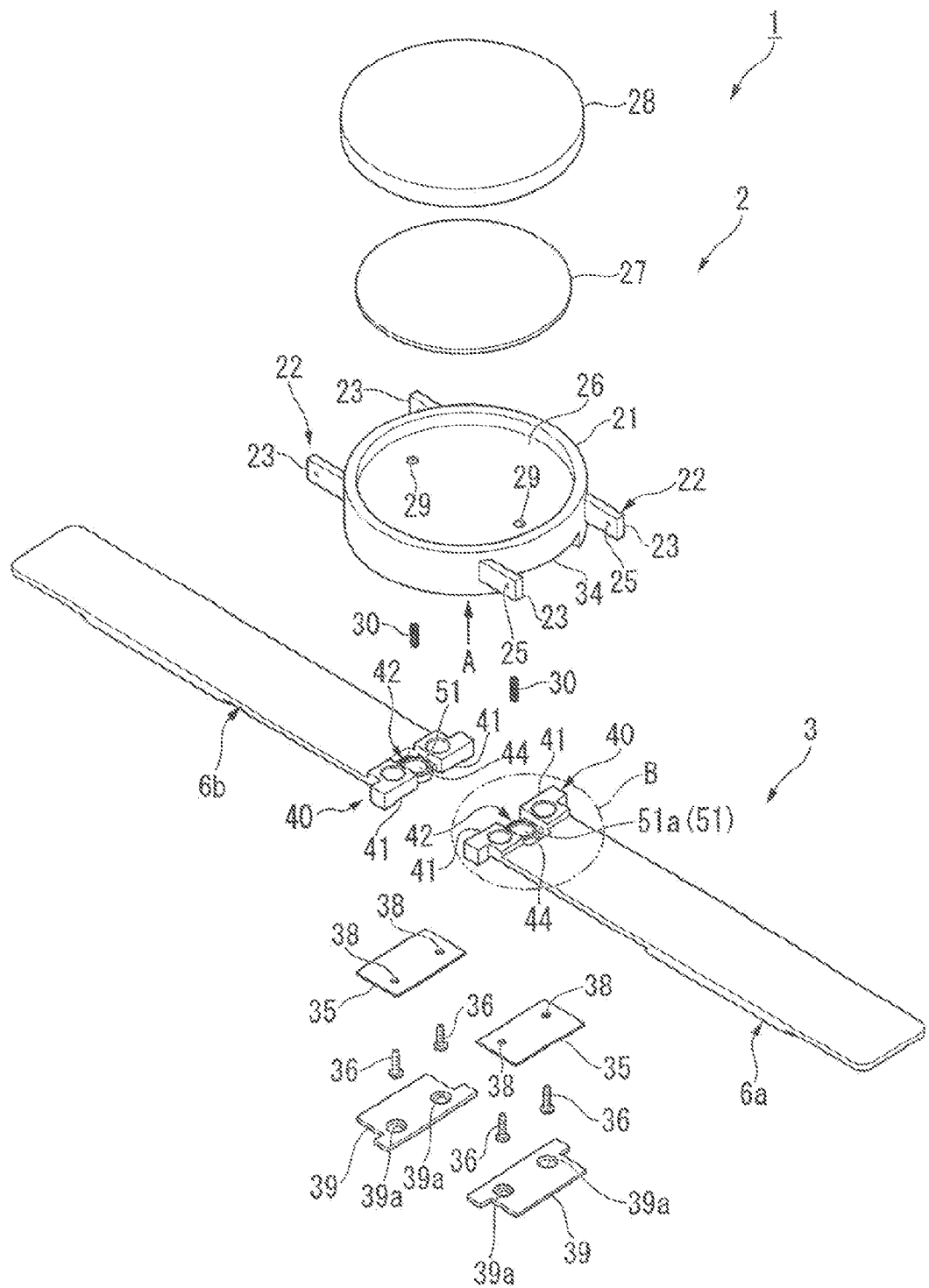
FIG. 4 is an exploded perspective view illustrating a main body portion and a heartbeat detection portion according to the first embed event of the present invention.
Figure 5:
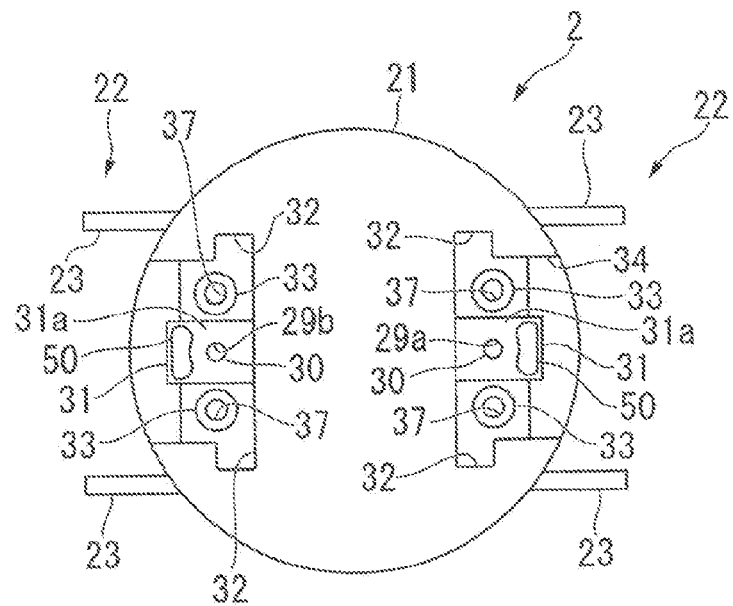
FIG. 5 is a diagram viewed from an arrow A of FIG. 4.
Figure 6:
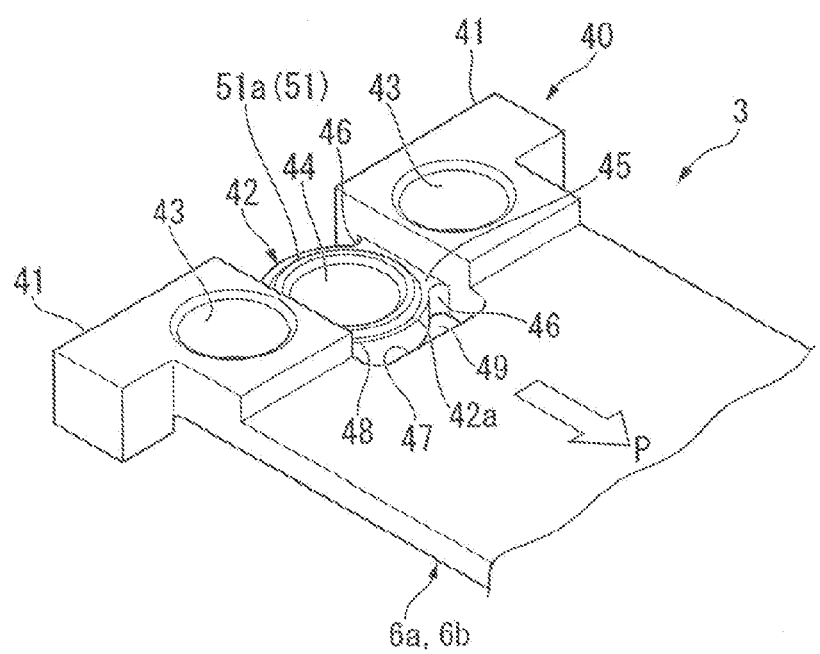
FIG. 6 is an enlarged view of a B portion of FIG. 4.
Figure 7:
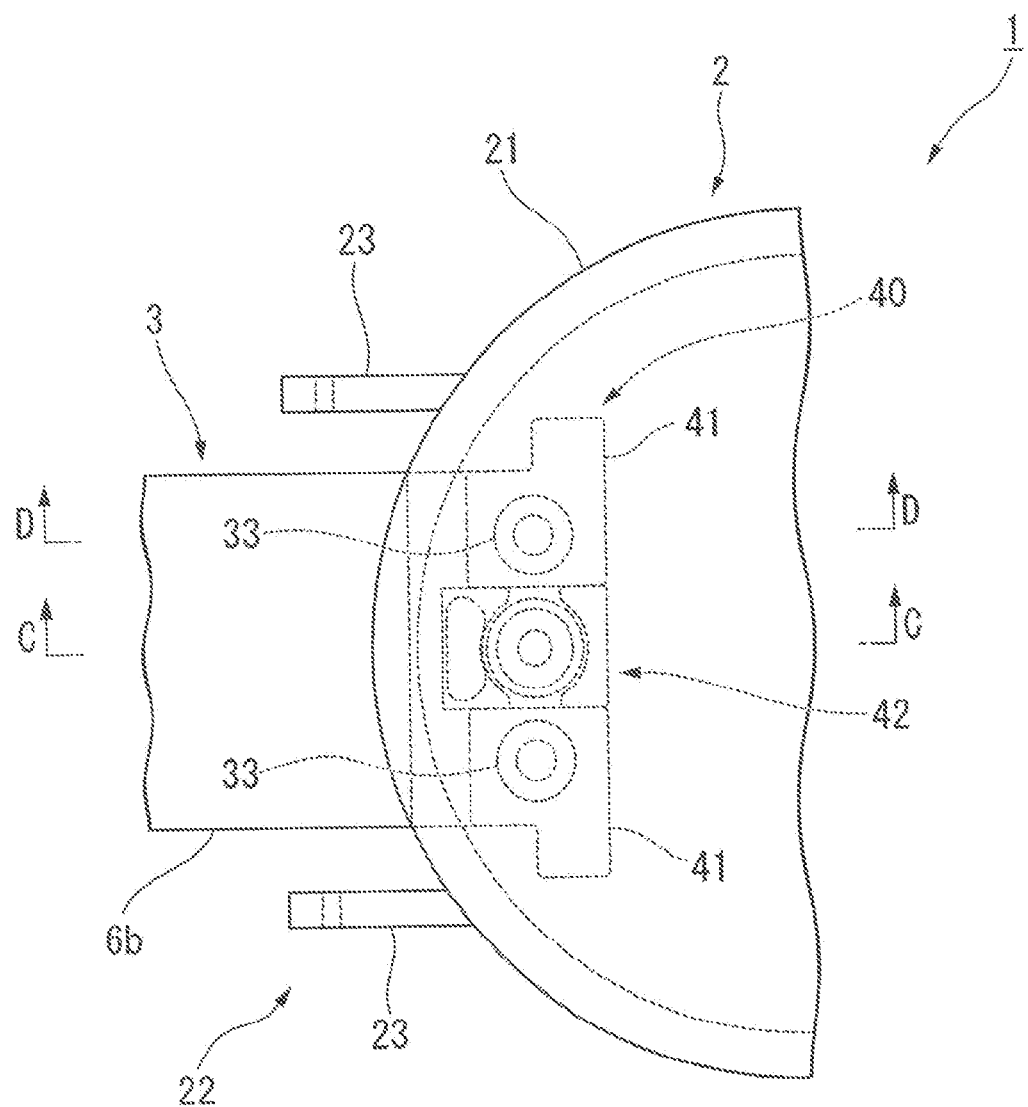
FIG. 7 is a partial plan view illustrating the main body portion and the heartbeat detection portion according to the first embodiment of the present invention.
Figure 8:
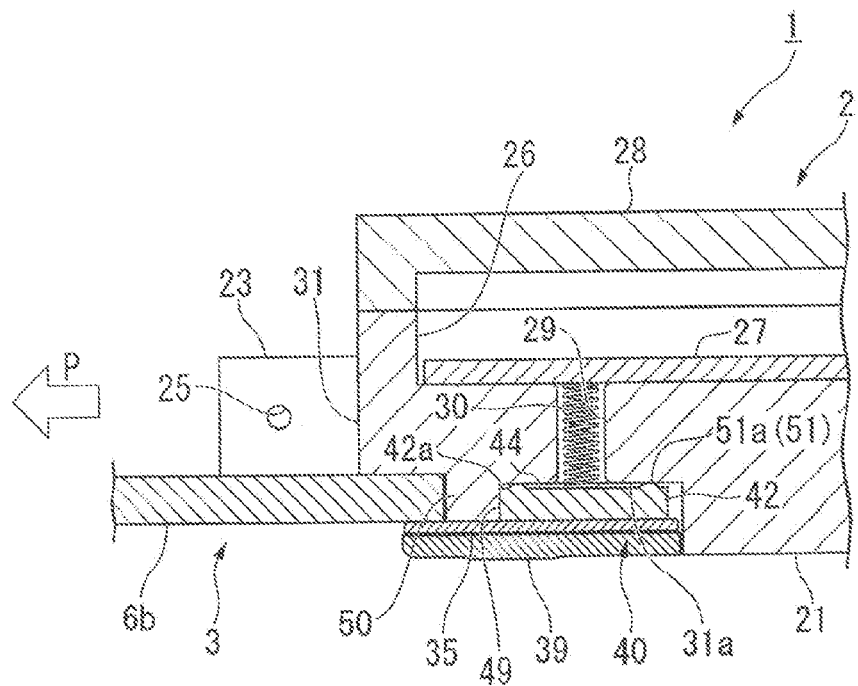
FIG. 8 is a cross-sectional view taken along the line C-C of FIG. 7.
Figure 9:
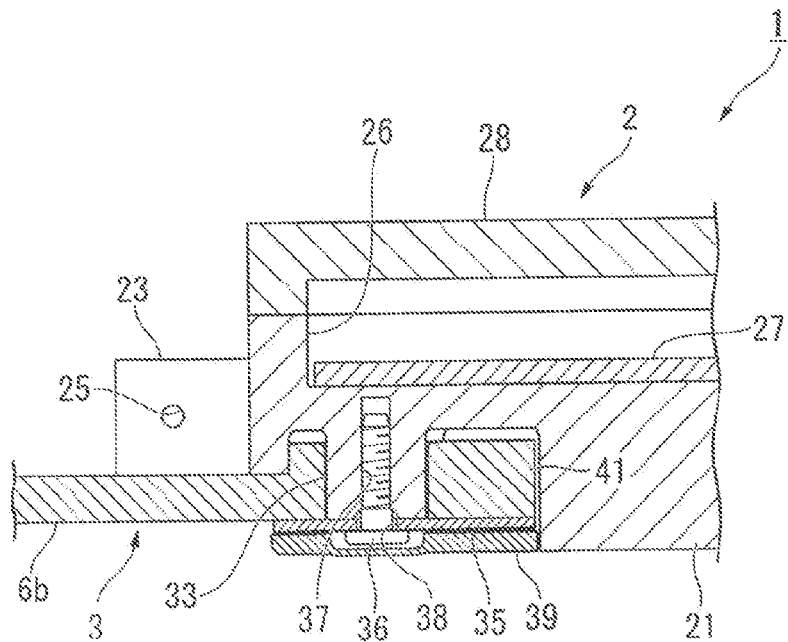
FIG. 9 is a cross-sectional view taken, along the line D-D of FIG. 7.

FIG. 4 is an exploded perspective view illustrating the main body portion 2 and the heartbeat detection portion 3, FIG. 5 is a diagram viewed iron an arrow A of FIG. 4, FIG. 6 is an enlarged view of a B portion of FIG. 4, FIG. 7 is a partial plan view illustrating the main body portion 2 and the heartbeat detection portion 3, FIG. 8 is a cross-sectional view taken along the line C-C of FIG. 7, and FIG. 9 is a cross-sectional view taken along the line D-D of FIG. 7.

As shown in FIGS. 3 to 9, the main body portion 2 includes a lower case 21 which is in a substantially disk shape. The lateral portions of the lower case 21 are respectively provided with connection members 22 for connecting the strap attaching and detaching members 12 and the main body portion 2 at both sides centered on the radial middle of the lower case 21.

The connection member 22 is constituted by a pair of support walls 23 and 23, formed upright from the lateral portion of the lower case 21, which face each other in the circumferential direction, and a shaft 24 provided so as to be laid between the support walls 23 and 23. The tip of the shaft 24 is configured to freely come in and out, and a through hole 25 capable of receiving the tip of the shaft 24 is formed in a place corresponding to the shaft 24 between the support walls 22 and 23.

Thereby, the shaft 24 is engaged with the support walls 23 and 23, and both 23 and 24 are integrated with each other. The hook portion 12b of the strap attaching and detaching member 12 is configured to be engagable with the shaft 24, and the main body portion 2 and the fixing band 4 is configured to be disengageable with each other.

In addition, in the front side of the lower case 21, a concave portion 26 is formed in the central large portion. A detection circuit board 27 is received in the concave portion 26. The detection circuit board 27 formed in a substantially disk shape so as to correspond to the shape of the concave portion 26. In addition, she detection circuit board 27 includes, for example, a wireless transmission portion and a transmitter circuit (all not shown), and performs wireless communication on the basis of a signal detected by the heartbeat detection portion 3.

Further, the concave portion 26 of the lower case 21 is provided with an upper case 28 so as to block an opening of the concave portion 26. The upper case 28 is termed in a substantially disk shape so as to correspond to the shape of she concave portion 26, and the diameter thereof is set so as to be substantially identical to the diameter of the lower case 21.

Meanwhile, each of the shapes of the lower case 21, the selection clients board 27, and the upper case 28 is not limited to a substantial disk shape, and various shapes can be adopted. For example, the lower case 21, the detection circuit board 27, and the upper case 28 can also be formed so that the external shapes thereof are substantially rectangular when seen in plan view.

In addition, through holes 29 and 29 passing through in the thickness direction close to each connection member 22 are formed in the concave portion 26 of the lower case 21, and a conductive member 30 is inserted into the through holes 29 and 29. The conductive member 30 is to electrically connect the detection circuit board 27 to the heartbeat detection portion 3, and is formed by, for example, a coil spring or the like.

Further, on the back side of the lower case 21, a positional displacement prevention convex portion 31 is integrally formed in an area corresponding to the through hole 29. The positional displacement prevention convex portion 31 is to prevent positional displacement of the main body portion 2 and the heartbeat detection portion 3 in a predetermined direction in cooperation with an insertion convex portion 50 (the details of the insertion convex portion 50 will be described later) formed in the positional displacement prevention convex portion 31, and is formed in a substantially rectangular shape in cross-section so as to be elongated along the extension direction (horizontal direction in FIG. 5) of the strap 8. The through hole 29 passes through the positional displacement prevention convex portion 31 in the thickness direction.

In addition, a pair of first receiving concave portions 32 and 32, which are substantially L-shaped when seen in plan view, for receiving the heartbeat detection portion 3 in the lower case 21 side are respectively formed on both sides of the positional displacement prevention convex portion 31 in the short-side direction. A positional displacement prevention protrusion 33 for preventing positional displacement between the main body portion 2 and the heartbeat decoction portion 3 in a predetermined direction is disposed upright integrally with the first receiving concave portion 32. A female screw portion 37 is engraved in the positional displacement prevention protrusion 33. A bolt 36 described later is threaded into the female screw portion 37, and is configured to be capable of fastening and fixing the heartbeat detection portion 3 to the main body portion 2.

Further, a second receiving concave portion 34 having a depth smaller than that of the first receiving concave portion 32 is formed at each connection member 22 side rather than the positional displacement prevention convex portion 31 and the first receiving concave portion 32. The second receiving concave portion 34 is also to receive the heartbeat detection portion 3 in the lower case 21 side, and is formed up to the lateral portion of the lower case 21. Thereby, the radial outside of the second receiving concave portion 34 is in an opened state, and the heartbeat detection portion 3 can be drawn into the lower case 21 from the outside.

The heartbeat detection portion 3 is placed in the first receiving concave portion 32 and she second receiving concave portion 34 which are formed in this manner, and a fixed reinforcing plate 35 is fastened and fixed to the lower case 21 using the bolt 36 from the top thereof, so that the main body portion 2 and the heartbeat detection portion 3 are integrated with each other. In the fixed reinforcing plate 35, a bolt insertion hole 38 is formed at a position corresponding to the female screw portion 37 engraved in she positional displacement prevention protrusion 33 of the lower case 21. The bolt 36 is inserted into the bolt insertion hole 38, and the fitted reinforcing plate 35 and the heartbeat detection portion 3 are fastened to each other.

In addition, a cover 39 is installed on the back side of the lower case 21 from the top of the fixed reinforcing plate 35. An opening 39a for avoiding interference with the head of the bolt 36 is formed in the cover 39. In addition, the cover 39 is formed so that the external shape thereof corresponds to the external shapes of the first receiving concave portion 32 and the second receiving concave portion 34. For this reason, the fixed reinforcing plate 35 and the bolt 36 can be completely covered by the cover 39, and the surface of the cover 39 and the surface of the lower case 21 can be disposed to be flush with each other, thereby allowing the aesthetics of the appearance to be improved.

The heartbeat detection portion 3 integrated with the main body portion 2 is constituted by a pair of electrodes 6a and 6b formed from a belt-like conductive elastomer.

Herein, as the conductive elastomer, for example, conductive silicon rubber mixed with carbon black, conductive rubber mixed with carbon black, conductive polyurethane rubber mixed with carbon black, or the like can be used.

In each of the electrodes 6a and 6b, a connection structure 40 is integrally formed at one end on the main body portion 2 side in the long-aids direction. The connection structure 40 is to connect each of the electrodes 6a and 6b so the main body portion 2 and to electrically connect the detection circuit board 27 received in the main body portion 2 to the electrodes 6a and 6b, and is formed from conductive elastomer similarly to the electrodes 6a and 6b.

In the connection structure 40, a pair of mechanical connection convex portions 41 and 41 formed in a substantially L-shape in cross-section so as to be capable of placing each of the first receiving concave portions 32 and 32 of the lower case 21, and an electrical connection circular plate 42 formed between the mechanical connection convex portions 41 and 41 and in an area corresponding to the positional displacement prevention convex portion 31 or the lower case 21 are formed integrally with each other.

In the mechanical connection convex portion 41, an insertion hole 43 capable of inserting the positional displacement prevention protrusion 33 is formed at a position corresponding to the positional displacement prevention protrusion 33 of the lower case 21.

The mechanical connection convex portions 41 and 41 are respectively placed in the first receiving concave portions 32 and 32 of the lower case 21, and the positional displacement prevention protrusion 33 of the lower case 21 is inserted into each insertion hole 43 of the mechanical connection convex portions 41 and 41, thereby preventing displacement of the mechanical connection convex portion 41 with respect to the lower case 21.

On the other hand, the electrical connection circular plate 42 is disposed so that the radial center thereof is located coaxially with the through holes 29a and 29b formed in the positional displacement prevention convex portion 31 of the lower case 21. That is, the radially central portion of the electrical connection circular plate 42 is formed as an electrical connection portion 44 which comes into contact with the conductive member 30 inserted into the through hole 29, and by which the electrodes 6a and 6b and the detection circuit board 27 are electrically connected to each other.

In addition, a sealing portion 51 in integrally for nod at an end face 42a of the electrical connection circular plate 42 on the main body portion 2 side so as to surround the periphery of the electrical connection portion 44. The sealing portion 51 is configured such that a seal main body 51a which is formed in a substantially triangular shape in cross-section is formed in a substantially circular-rang shape when seen in plan view so as to surround the periphery of the electrical connection portion 44.

Further, both sides of the electrical connection circular plate 42 are connected to the mechanical connection convex portions 41 through a connection portion 45 with the electrical connection portion 44 interposed therebetween. The connection portion 45 is integrally formed together with the mechanical connection convex portions 41 and the electrical connection circular plate 42. Both sides thereof in the width direction are slightly resected and constricted portions 46 are formed. The rigidity of the connection portion 45 is set to be weaker than that of the mechanical connection convex portion 41 or the electrical connection portion 44.

In addition, the thickness of the electrical connection circular plate 42 is set to be slightly smaller than the thickness of the electrodes 6a and 6b. Further, a concave portion 47 is formed between the mechanical connection convex portions 41 and 41 at the end of the electrodes 6a and 6b on the connection structure 40 side.

According to such a configuration, a fitting concave portion 48 is formed by the mechanical connection convex portion 41 and the electrical connection circular plate 42. The positional displacement prevention, convex portion 31 of the loner case 21 is fitted into the fitting concave portion 48. In addition, a slit 49 serving as the concave portion 47 is formed at one end of the electrodes 6a and 6b in the long-side direction.

The positional displacement prevention convex portion 31 of the lower case 21 is formed so as to be fitted into the fitting concave portion 48, and is formed so as so cover the slit 49. An end face 31a of the positional displacement prevention convex portion 31 and an end face 42a of the electrical connection circular plate 42 come close to each other. In addition, the insertion convex portion 50 capable of being inserted into the slit 49 is formed in the positional displacement prevention convex portion 31. Thereby, displacement of the relative position between the electrodes 6a and 6b and the main body portion 2 is prevented.

Based on such a configuration, when the connection structure 40 of each of the electrodes 6a and 6b is placed in the first receiving concave portion 32 and the second receiving concave portion 34 of the lower case 21, and the fixed reinforcing plate 35 is fastened and fixed to the lower case 21 from the top thereof using the bolt 36, the conductive member 30 provided to the lower case 21 and the electrical connection portion 44 of the connection structure 40 come into contact with each other, and the conductive member 30 and the electrical connection portion 44 are electrically connected to each other. In addition, the sealing portion 51 formed in the periphery of the electrical connection portion 44 is pressed and squashed to the positional displacement prevention convex portion 31 of the lower case 21. Moreover, since the sealing portion 51 is formed from conductive elastomer, it is compressible and can be pressed reliably and easily, and sealing of the electrical connection portion 44 from the outside is secured reliably.

In this manner, after the heartbeat detection portion 3 constituted by the main body portion 2 and the electrodes 6a and 6b is integrally formed, the strap attaching and detaching member 12 of the fixing band 4 wound around the chest of the user U and the connection member 22 of the main body portion 2 are caused to be engaged with each other. Thereby, the mounting of the heartbeat measurement device 1 to the chest of the user U is completed. In a state where the heartbeat measurement device 1 is installed, each of the electrodes 6a and 6b is pressed down by the strap 8 from above. An electro-cardiac signal generated in association with a heartbeat is detected by the pair of electrodes 6a and 6b. The detection circuit board 27 of the main body portion 2, for example, wirelessly communicates the electro-cardiac signal detected by the pair of electrodes 6a and 6b.

Herein, the main body portion 2 and the electrodes 6a and 6b are separate from each other, each of the electrodes 6a and 6b is installed on the loner case 21 of the main body portion 2 through the connection structure 40, and the main body portion 2 and the electrodes 6a and 6b are formed integrally with each other. For this reason, there is concern of it being difficult to cause a gap between the lower case 21 and the electrodes 6a and 6b not to be generated at all, and thus sweat from the human body or foreign substances infiltrate through this gap. When sweat from the human body or foreign substances infiltrate, the conductive member 30 may be corroded, or the state of the connection between the electrical connection portion 44 and the conductive member 30 may be deteriorated. However, since the sealing portion 31 is integrally formed in the periphery of the electrical connection portion 44, and sealing of the electrical connection portion 44 from the outside is secured, sweat from the human body or foreign substances are prevented from infiltrating.

Therefore, according to the above-mentioned first embodiment, the main body portion 2 and the heartbeat detection portion 3 are formed integrally with each other, and the strap 8 of the fixing band 4 is installed on the main body portion 2. Therefore, while the main body portion 2 and the heartbeat detection portion 3 are formed detachably to the fixing bend 4, the sealing portion 51 is provided in the periphery of the electrical connection portion 44, so that it is possible to prevent a defective connection between the electrical connection, portion 44 and she conductive member 30 from occurring. For this reason, it is possible to prevent the defective detection of the heartbeat measurement device 1 from occurring while securing good maintenance of the heartbeat measurement device 1.

In addition, the heartbeat detection portion 3 is integrally provided to the main body portion 2, and the fixing band 4 is detachably provided to the main body portion 2, so that it is possible to separate the main body portion 2 and the heartbeat detection portion 3 from the fixing band 4 in a state where the main body portion 2 and the heartbeat detection portion 3 are formed integrally with each other. For this reason, it is possible to easily perform cleaning of only the fixing band 4. Thus, it is possible to reliably prevent defects from occurring in electrical parts such as the electrodes 6a and 6b, the conductive member 30, and the electrical connection portion 44.

In addition, since the sealing portion 51 is integrally formed in the electrical connection circular plate 42, she number of parts for securing sealing around the electrical connection portion 44 does not increase, and thus it is possible to prevent ease of assembly from being deteriorated, and to reduce costs.

Further, the heartbeat detection portion 3 is constituted by a pair of electrodes 6a and 6b formed from a belt-like conductive elastomer, so that when it is pressed down by the strap 8 from the top of each of the electrodes 6a and 6b, the electrodes 6a and 6b are easily elastically deformed. For this reason, it is possible to increase adhesion or the electrodes 6a and 6b to the chest of the user U, and to increase detection accuracy of an electro-cardiac signal using a pair of electrodes 6a and 6b.

The sealing portion 51 formed integrally with the electrical connection circular plate 42 is also formed from conductive elastomer, and thus it is possible to increase adhesion of the sealing portion 51 by elastically deform the sealing portion 51. For this reason, it is possible to more reliably increase sealing of she electrical connection portion 44.

In addition, since the fining band 4 is installed on the main body portion 2, the fixing band 4 and the heartbeat detection portion 3 are separated from each other, and each of the electrodes 6a and 6b of the heartbeat detection portion 3 is pressed down to the chest of the user U by the strap 8 from the top thereof. For this reason, it is possible to suppress the application of the external force such as the pulling of each of the electrodes 6a and 6b.

However, even in so on a configuration, it is also considered that external force is applied to each of the electrodes 6a and 6b. Herein, operations in a case where external force in the tensile direction is applied to the electrodes 6a and 6b will be described with reference to FIGS. 6 and 8.

As shown in FIGS. 6 and 8, when external force P in the tensile direction is applied to the electrodes 6a and 6b, a load is transmitted to the connection structure 40 formed integrally with one end of the electrodes 6a and 6b in the long-side direction. More specifically, a road is transmitted to the mechanical connection convex portion 41 formed integrally with the electrodes 6a and 6b. At this time, the direction of a load on the mechanical connection convex portion 41 is a direction of the electrodes 6a and 6b in the long-side direction.

Herein, the electrical connection circular plate 42 connected to the mechanical connection convex portion 41 through the connection portion 45 is disposed between each of the mechanical connection convex portions 41 and 41, and the array direction of the mechanical connection convex portions 41 and 41 and the electrical connection circular plate 42 becomes a direction intersecting substantially at a right angle to the direction of a load on the mechanical connection convex portion 41. Moreover, a constricted portion 46 is formed in the connection portion 45, and the rigidity of the connection portion 45 is set to be weaker than that of the mechanical connection convex portion 41 or the electrical connection portion 44. For this reason, the connection portion 45 is easily classically deformed, and the load on the mechanical connection convex portion 41 is not easily transmitted to the electrical connection circular plate 42. Thus, even when the external force P is applied to the electrodes 6a and 6b, it is possible to stabilize the state of the connection between the electrical connect ion portion 44 of the electrical connection circular plate 42 and the conductive member 30.

Meanwhile, in the above-mentioned first embodiment, a case has been described in which the sealing portion 51 is formed in a substantially triangular shape in cross-section, and in a substantially circular-ring shape when, seen in plan view. However, without being limited thereto, the sealing portion may protrude from the end face 42a of the electrical connection circular plate 42 on the main body portion 2 side, and may be formed so as to surround the periphery of the electrical connection portion 44. For example, the sealing portion may be formed in a substantially semicircular shape in cross-section, and in a substantially rectangular shape when seen in plan view.

In addition, in the above-mentioned first embodiment, a case has been described in which she sealing portion 51 is formed integrally with the electrical connection circular plate 42. However, without being limited thereto, the electrical connection circular plate 42 and the sealing portion 51 may be formed separately.

Further, instead of providing the sealing portion 51 in the electrical connection circular plate 42, the sealing portion may be protrusively provided in an area corresponding to the periphery of the electrical connection portion 44 in the positional displacement prevention convex version 31 of the lower case 21. In this case, the electrical connection circular plate 42 is pressed by the searing portion of the lower case 21, and thus it is possible to secure sealing of the electrical connection portion 44 by squashing the electrical connection circular plate 42.

In each of the above-mentioned cases, the sealing portion 51 surrounds a peripheral portion of the electrical connection portion 44 and is compressed or squashed between the main body portion 2 and the electrical connection portion 44.

In the above-mentioned first embodiment, a case has been described in which in mounting the heartbeat measurement device 1 to the chest of the user U, the fixing band 4 is wound around the chest of the user U, and then the strap attaching and detaching member 12 of the fixing band 4 and the connection member 22 of the main body portion 2 are caused to be engaged with each other. However, without being limited thereto, for example, the strap attaching and detaching member 12 of the fixing band 4 and the connection member 22 of the main body portion 2 may be caused to be engaged with each other, and then the heartbeat measurement device 1 may be mounted by winding the fixing band 4 around the chest of the user U.

In addition, in the above-mentioned first embodiment, a case has been described in which the conductive member 30 for electrically connecting the detection circuit board 27 to the electrical connection portion 44 is formed by, for example, a coil spring or the like. However, without being limited thereto, a conductive pin 60 may be used instead of the coil spring. Hereinafter, more specific aspects will be described.

First Modified Example of First Embodiment

Figure 10:
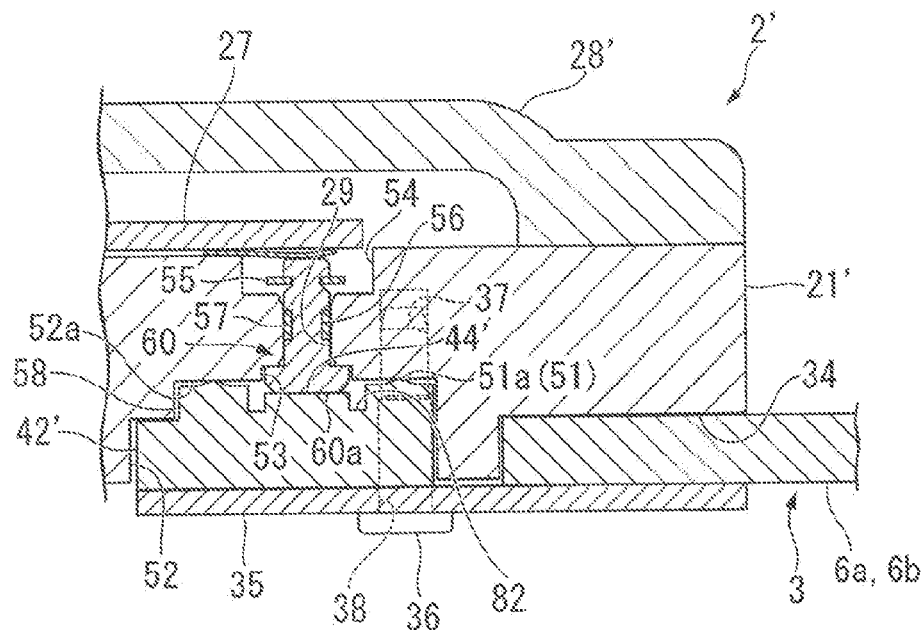
FIG. 10 is a cross-sectional view illustrating a main body portion according to a first modified example in the first embodiment of the present invention.

FIG. 10 is a cross-sectional view illustrating a main body portion 2' according to a first modified example of the first embodiment. Meanwhile, the same components as those of the above-mentioned first embodiment are designated by the same reference signs, and a description thereof will be omitted (the same is true of the following modified example and the Embodiment).

As shown in the came drawing, in the first modified example of the first embodiment, the main body portion 2' includes a lower case 21' and an upper case 28'. The following basic configuration of the modified example is the same as that of the above-mentioned first embodiment (the same is true of the following second modified example of the first embodiment): the detection circuit board 27 is provided within the lower case 21'; the electrodes 6a and 6b constituting the heartbeat detection portion 3 are integrally connected to the lower case 21', and the like.

Herein, a concave portion 32 receiving an electrical connection circular plate 42' in the back side (lower side in FIG. 10) is formed at a position corresponding to the through hole 29 of the lower case 21'. Further, a concave portion 53 receiving a head 60a of the conductive pin 60 inserted into the through hole 29 is formed on a bottom 52a of the concave portion. In addition, a diameter expansion portion 54 of which the diameter is expanded due to the step difference is formed at a position corresponding to the through hole 29 in the surface on the front side (upper side in FIG. 10) of the lower case 21'. The diameter expansion portion 54 is to avoid interference with a retaining ring 55 installed on the tip of the conductive pin 60 after the conductive pin 60 is inserted into the through hole 29 from the back side.

In addition, a packing groove 56 is formed in the conductive pin 60 over the whole circumference, and a packing 57 is mounted thereto. Thereby, sealing is secured between the through hole 29 and the conductive pin 60.

On the other hand, in the electrical connection circular plate 42', the sealing portion 51 is integrally formed on a convex portion 58 formed upright in a ring shape when seen in plan view. Thereby, when the electrical connection circular plate 42' is installed on the lower case 21', it is possible to easily compressively deform the convex portion 58 together with the sealing portion 51, and to increase adhesion between the electrical connection circular plate 42' and the lower case 21'. In this case, sealing is secured only by the main body portion 2 in addition to sealing of the electrical connection portion 44', and thus it is possible to further increase sealing as the heartbeat measurement device 1.

In addition, in the electrical connection circular plate 42', a ring-shaped groove 82 is formed on the radially inner side of the convex port ion 58, and the inside of the groove 82 is used as she electrical connection portion 44'. That is, a groove 82 is formed between the electrical connection portion 44' and the sealing portion 51. Thereby, the electrical connection portion 44' is protrusively formed. In addition, the protrusion height of the electrical connection portion 44' is lower than that of the convex portion 58, and is set to a height at which the electrical connection portion 44' is capable of being pressed by the head 60a of the conductive pin 60 when the electrical connection circular plate 42' is installed on the lower case 21'. Thereby, it is possible to cause the conductive pin 60 and the electrical connection portion 44' to adhere tightly to each other, and to reduce contact resistance between the two.

Meanwhile, the groove 82 may not be formed in a ring shape, and may be formed intermittently on the radially inner side of the convex portion 58 along the circumferential direction.

Therefore, according to the first modified example of the above-mentioned first embodiment, contact resistance of the electrical connection portion 44' is reduced in addition to the same effect as that of the above-mentioned first embodiment, and thus it is possible to more reliably prevent sweat from the human body or foreign substances from infiltrating into the electrical connection portion 44' without damaging adhesion of the sealing portion 51 to the lower case 21'.

In addition, even when external force (for example, load pulled in the long-side direction) is applied to the electrodes 6a and 6b by the formation of the groove 82 in the electrical connection circular plate 42', and the sealing portion 51 is displaced, the displacement of the electrical connection portion 44' is reduced, and thus it is possible to stabilise the state of the contact between the electrical connection portion 44' and the conductive pin 60.

Figure 11:
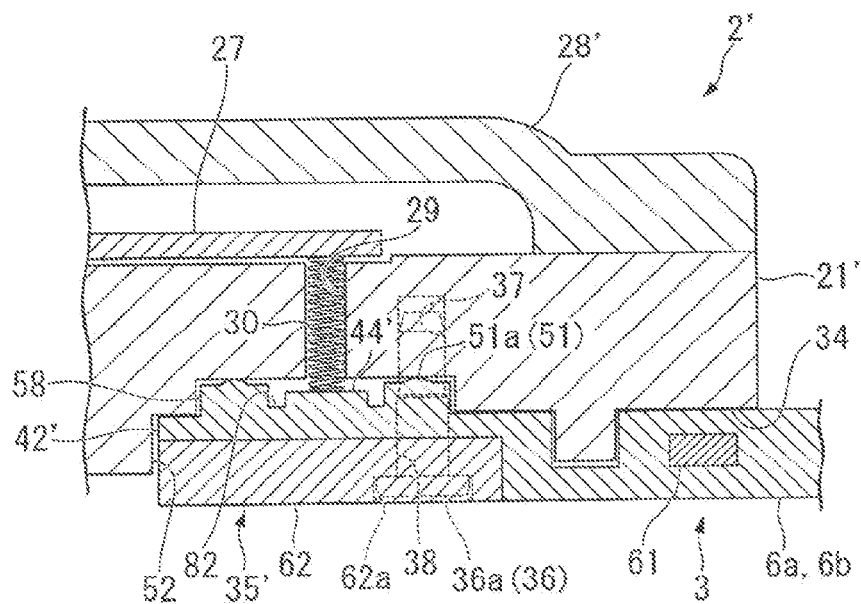
FIG. 11 is a cross-sectional view illustrating a main body portion according to a second modified example in the first embodiment of the present invention.

Further, in the above-mentioned first embodiment, a case has been described in which in installing the electrodes 6a and 6b of the heartbeat detection portion 3 on the main body portion 2, the fined reinforcing plate 35 is placed from the top of the electrodes 6a and 6b, and the fixed reinforcing plate 35 and each of the electrodes 6a and 6b are fastened to each other by the bolt 36. However, without being limited thereto, as shown in FIG. 11, the electrodes 6a and 6b and a fixed reinforcing plate 35' may be formed integrally with each other, and the structure formed in this manner may be installed on the main body portion 2'. More specific aspect will be described below.

Second Modified Example of First Embodiment

FIG. 11 is a cross-sectional view illustrating the main body portion 2' according to a second modified example of the first embodiment.

As shown in the same drawing, the electrodes 6a and 6b are formed thick by the thickness equivalent to that of the fined reinforcing plate 35 according to the above-mentioned first embodiment. The fixed reinforcing plate 35' according to the second modified example of the first embodiment is insert-molded on the electrodes 6a and 6b.

The fixed reinforcing plate 35' includes a first plate portion 61 disposed at a position corresponding to the concave portion 34 of the lower case 21' and a second plate portion 62 disposed at a position corresponding to the concave portion 52 of the lower case 21'.

The first plate portion 61 is buried in the electrodes 6a and 6b. In addition, she second plate portion 62 is disposed so as to be exposed to the back side of the electrodes 6a and 6b. Further, the thickness of the second plate portion 62 is set to a thickness capable of receiving a head 26a of the bolt 36, and a concave portion 62a receiving the head 36a is formed at a position corresponding to the bolt 36.

According to such a configuration, in addition to the same effect as that of the first modified example of the above-mentioned first embodiment, it is possible to reduce the number of parts, and to reduce the number of assembly processes and reduce costs.

Second Embodiment

Heartbeat Measurement Device

Next, reference will be made to FIG. 1 to describe a second embodiment of the present invention on the basis of FIGS. 12 to 17.

Figure 12:
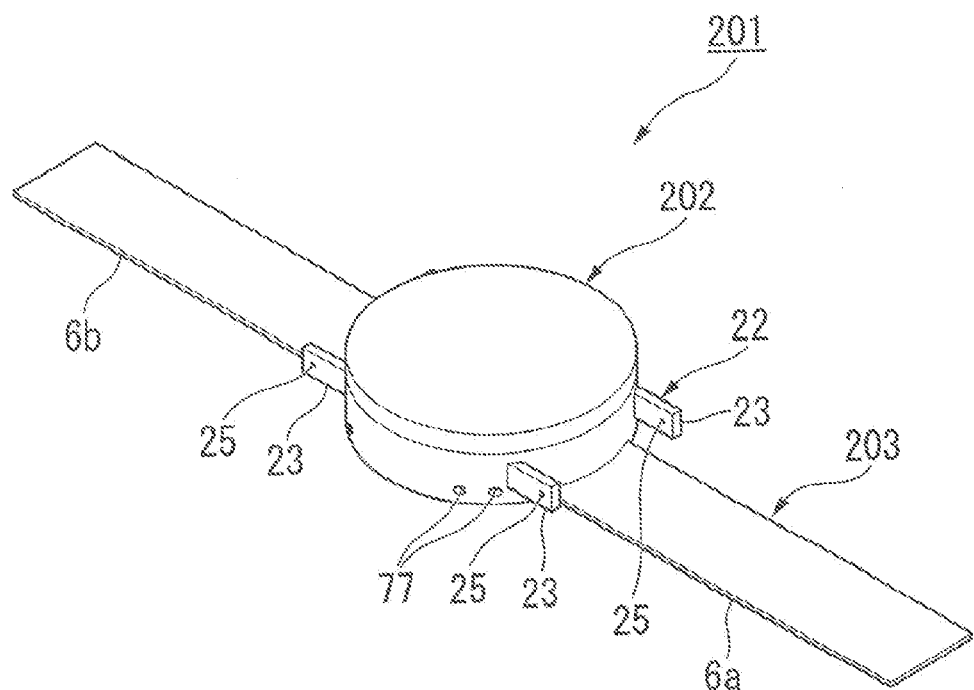
FIG. 12 is a perspective view illustrating a main body portion and a heartbeat detection portion according to a second embodiment of the present invention.
Figure 13:
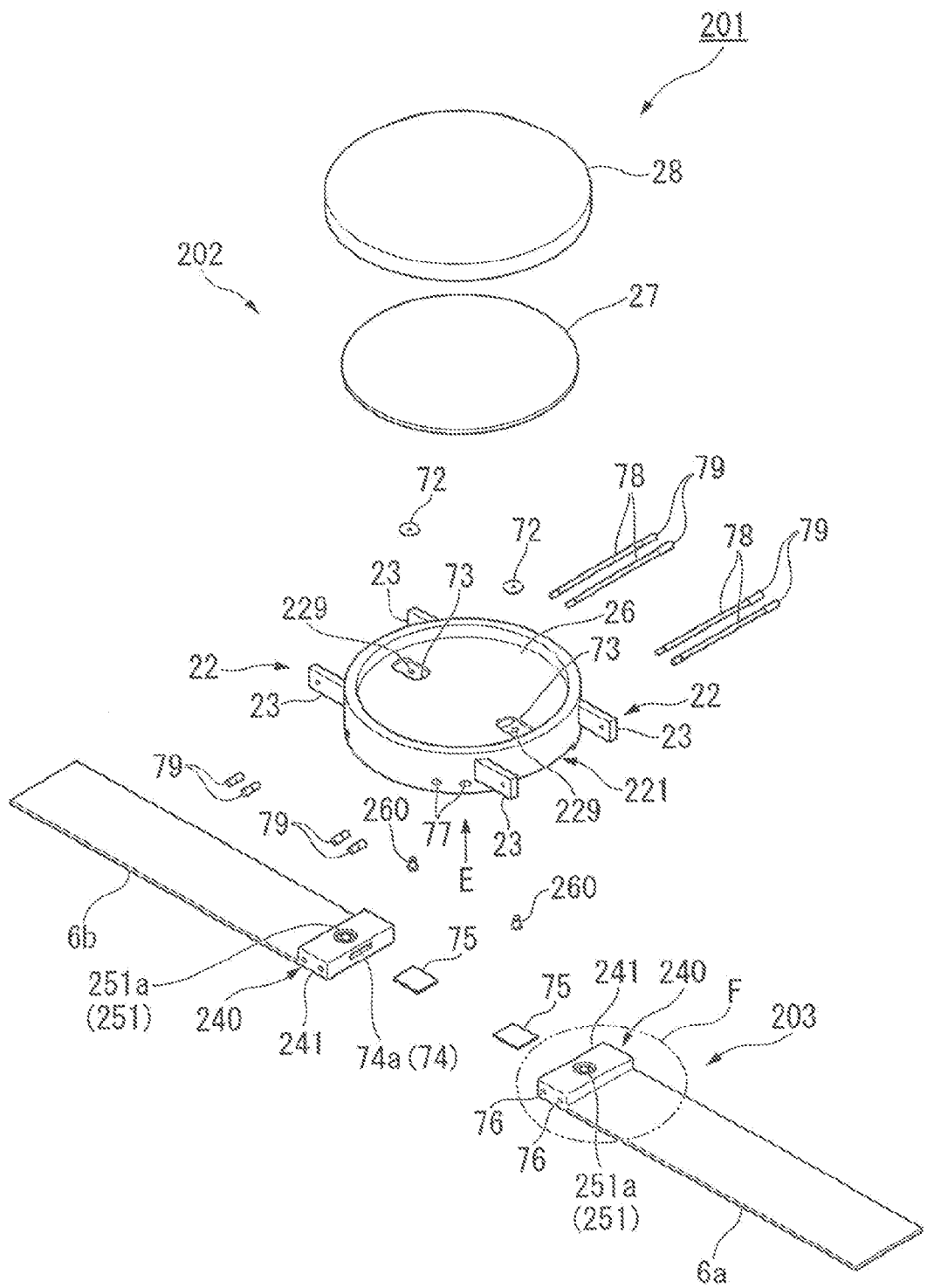
FIG. 13 is an exploded perspective view illustrating the main body portion and the heartbeat detection portion according to the second embodiment of the present invention.
Figure 14:
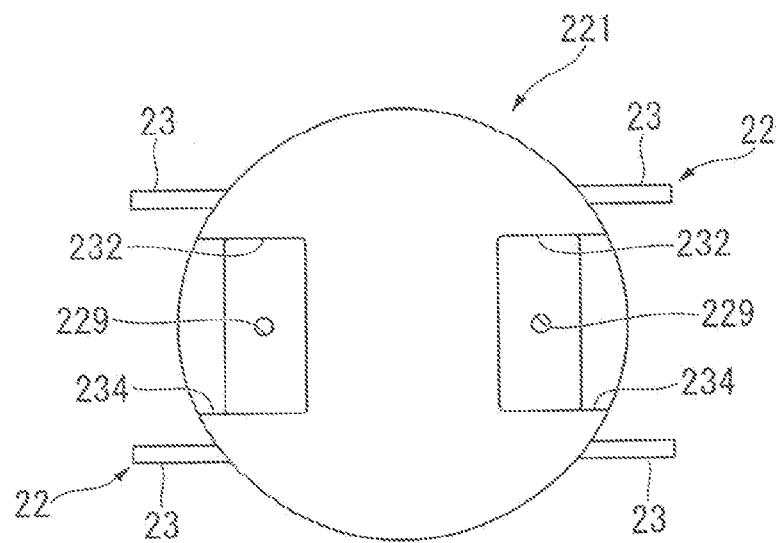
FIG. 14 is a diagram viewed from an arrow E of FIG. 13.
Figure 15:
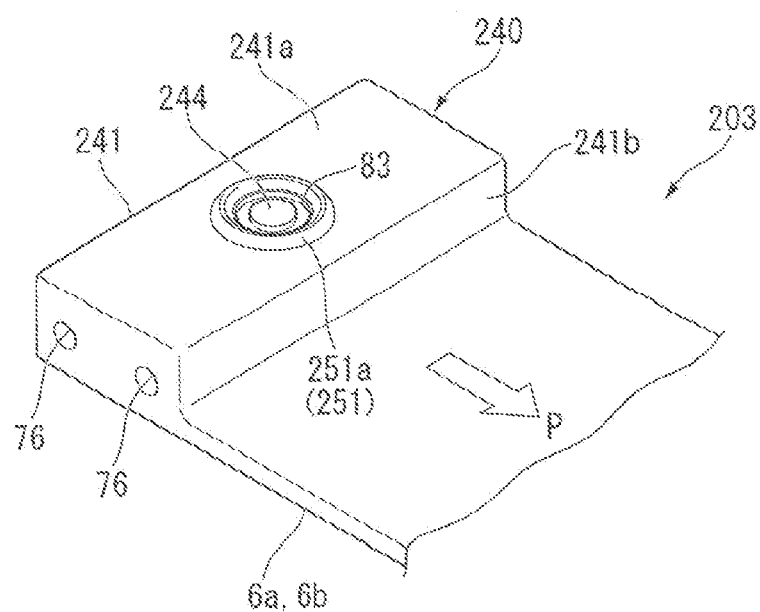
FIG. 15 is an enlarged view of an F portion of FIG. 13.
Figure 16:
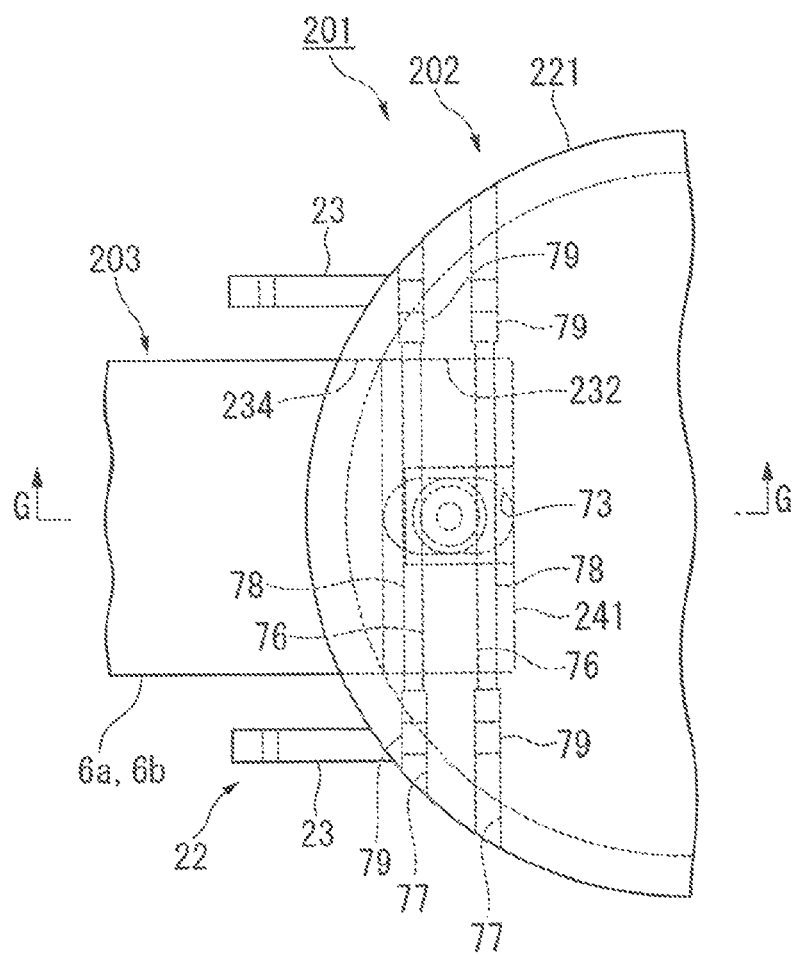
FIG. 16 is a partial plan view illustrating the main body portion and the heartbeat detection portion according to the second embodiment of the present invention.
Figure 17:
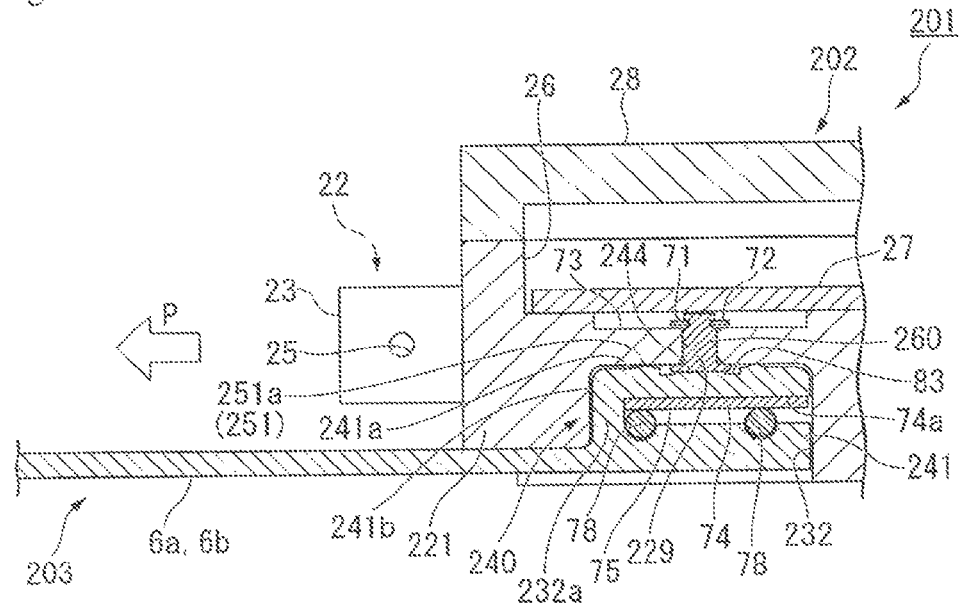
FIG. 17 is a cross-sectional view taken along the line G-G of FIG. 16.

FIG. 12 is a perspective view illustrating a main body portion 202 and a heartbeat detection portion 203 which constitute a heartbeat measurement device 201 according to the second embodiment, FIG. 13 is an exploded perspective view illustrating the main body portion 202 and the heartbeat detection portion 203 which constitute the heartbeat measurement device 201, FIG. 14 is a diagram viewed from an arrow E of FIG. 13, FIG. 15 is an enlarged view of an F portion of FIG. 13, FIG. 16 is a partial plan view illustrating the main body portion 202 and the heartbeat detection portion 203, and FIG. 17 is a cross-sectional view taken along the lice G-G of FIG. 16.

As shown FIGS. 1, 12, and 13, in the second embodiment, the heartbeat measurement device 201 includes the stain body portion 202, the heartbeat detection portion 203 formed integrally with the mum body portion 202, and the fixing band 4 which mounts the main body portion 202 and the heartbeat detection portion 203 to the chest of the user U. The following basic configuration of the embodiment is the same as the above-mentioned first embodiment: the fixing band 4 and the main body portion 202 are detachable with each other through the strap attaching and detaching member 12 and the connection member 22; the heartbeat detection portion 203 and the fixing band 4 are separated from each other; the heartbeat detection portion 203 includes a pair of electrodes 6a and 6b; when the heartbeat measurement device 201 is mounted, the electrodes 6a and 6b are pressed down by the strap 8 from above; the main body portion 202 includes a lower case 221, the defection circuit board 27 provided to the concave portion 26 formed in she lower case 221, and the upper case 28 provided so as to block the concave portion 26; the detection circuit board 27 and each of the electrodes 6a and 6b are electrically connected to each other, and the like.

Herein, the difference between the first embodiment and the second embodiment is that a connection structure between the main body portion 2 and the heartbeat detection portion 3 according to the first embodiment and a connection structure between the main body portion 202 and the heartbeat detection portion 203 according to the second embodiment are different iron each other.

More specifically, as shown in FIGS. 12 to 17, through holes 229 and 229 passing through in the thickness direction close to each connection member 22 are formed in the concave portion 26 of the lower case 221. A conductive pin 260 is inserted into the through hole 229 from the back side of the lower case 221.

A retaining ring groove 71 is formed on the tip of the conductive pin 260. After the conductive pin 260 is inserted into the through hole 229, a retaining ring 72 is mounted to the retaining ring groove 71. Thereby, the conductive pin 260 is prevented from falling out from the through hole 229. In addition, in the concave portion 26 of the lower case 221, a counter-boring portion 73 receiving the retaining ring 72 is formed in an area corresponding to the through hole 229, and the tip of the conductive pin 260 can be prevented from protruding the concave portion 26 of the lower case 221.

Further, on the back side of the lower case 221, a first receiving concave portion 232 is formed in an area corresponding to the through hole 229. The first receiving concave portion 232 is to receive the heartbeat detection portion 203, and is formed in a substantially rectangular shape when seen in plan view so as to be elongated in the width direction of the electrodes 6a and 6b constituting the heartbeat detection portion 203.

In addition, a second receiving concave portion 234 having a depth smaller than that of the first receiving concave portion 232 is formed on each connection member 22 side rather than the first receiving concave portion 232. The second receiving concave portion 234 extends up to the lateral portion of the lower case 221 with the same width as she width of the first receiving concave portion 232 in the long-side direction. Thereby, the radial outside of the second receiving concave portion 234 is in an opened state. The electrodes 6a and 6b are disposed in the second receiving concave portion 234.

Meanwhile, the width of the first receiving concave portion 232 and the width of the second receiving concave portion 234 may not be set to be the same as each other.

On the other hand, in each of the electrodes 6a and 6b, a connection structure 240 is integrally formed at one end on the main body portion 202 side in the long-side direction. The connection structure 240 is to connect each of the electrodes 6a and 6b to the main body portion 202, and to electrically connect the detection circuit board 27 received in the main body portion 202 to the electrodes 6a and 6b. The connection structure 240 includes a mechanical connection convex portion 241 formed in a substantially rectangular shape in cross-section so as to be elongated in the width direction of each of the electrodes 6a and 6b, as corresponding to the first receiving concave portion 232 of the lower case 221. The mechanical connection convex portion 241 is formed integrally with one end of each of the electrodes 6a and 6b in the long-side direction, and is received in the first receiving concave portion 232, so that the swain body portion 202 and the heartbeat detection portion 203 are integrated with each other.

In the mechanical connection convex portion 241, a reinforcing plate receiving groove 74 having an opening 74a is formed at the end face on the main body portion 202 side (right side in FIG. 17). A reinforcing plate 75 is received in the reinforcing plate receiving groove 74

In addition, in the mechanical connection convex portion 241, two through holes 76 and 76 on the convex portion side passing through along the width direction of the electrodes 6a and 6b are disposed in parallel along the long-side direction of the electrodes 6a and 6b. Further, each through hole 76 on the convex portion side is formed so as to be in communication with the reinforcing plate receiving groove 74.

In addition, in the lower case 221, when the mechanical connection convex portion 241 is received in the first receiving concave portion 232, a through hole 77 on the case side is formed at a position corresponding to the through hole 76 on the convex portion side of the mechanical connection convex portion 241. The internal diameter of the through hole 77 on the case side is set to be slightly larger than the internal diameter of the through hole 76 on the convex portion side.

A fixing pin 78 is inserted into she through hole 76 on the convex portion side and the through hole 77 or the case side. The length of the fixing pin 78 is larger than the length of the mechanical connection convex portion 241 in the long-side direction, and is set to a length in which the fixing pin does not protrude from the lateral portion of the lower case 221. A fixing pipe 79 is fitted and fixed onto both ends of the fixing pin 78.

Herein, the diameter of the fixing pin 78 is set to be substantially identical to the internal diameter of the through hole 76 on the convex portion side. In addition, the diameter of the fixing pipe 79 is set to be substantially identical to the internal diameter of the through hole 77 on the case side. That is, after the mechanical connection convex portion 241 is received in the first receiving concave portion 232 of the lower case 221, a fixing pin 78 is inserted into the through hole 76 on the convex portion side through the through hole 77 on the case side, and the fixing pipe 79 inserted into the through hole 77 on the case side is fitted and fixed onto both ends of the fixing pin 78.

Since the diameter of the fixing pipe 79 is set to be larger than the internal diameter of the through hole 76 on the convex portion side, the fixing pipe 79 is fitted and fixed onto both ends or the fixing pin 78, and thus the movement of the fixing pin 78 to the failing-out direction is regulated. In addition, the fixing pin 78 is inserted into the through hole 76 on the convex portion side and the through hole 77 on the case side, so that each of the electrodes 6a and 6b is fixed to the loner case 221 through the fixing pin 78.

In addition, since the through hole 76 on the convex portion side is formed so as to be in communication with the reinforcing plate receiving groove 74, the reinforcing plate 75 is placed on the fixing pin 78 in a state where the fixing pin 78 is inserted into the through hole 76 on the convex port ion side. The groove width of the mechanical connection convex portion 241 in the thickness direction in the reinforcing plate receiving groove 74 is set so that the reinforcing plate 75 is brought into contact with the inner wall of the reinforcing plate receiving groove 74, in a state where the reinforcing plate 75 is placed on the fixing pin 78. Thereby, the rigidity of an end face 241a of the mechanical connection convex portion 241 on the main body portion 202 side (upper side in FIGS. 15 and 17) is increased.

In addition, in the end face 241a of the mechanical connection con vex portion 241, a ring-shaped groove 83 is formed in the periphery of a position corresponding to the conductive pin 260, and the inside of the groove 83 is used as an electrical connection portion 244. That is, the electrical connection portion 244 is provided in the central portion of the end face 241a of the mechanical connection convex portion 241. In addition, a ring-shaped sealing portion 251 is integrally formed in the periphery of the groove 83. That is, the sealing portion 251 is integrally formed so as to surround the periphery of the electrical connection portion 244. The sealing portion 251 is a component in which a seal main body 251a formed in a substantially triangular shape in cross-section is formed in a substantially circular-ring shape when seen in plan view so as to surround the periphery of the electrical connection portion 244.

Herein, when the electrodes 6a and 6b are installed on the lower case 221, the electrical connection portion 244 and the sealing portion 251 are pressed and squashed to the bottom of the first receiving concave portion 232 of the lower case 221. Since the rigidity of the end face 241a of the mechanical connection convex portion 241 is increased by the reinforcing plate 75, the sealing portion 251 formed so as to protrude from the end face 241a of the mechanical connection convex portion 241 is easily squashed.

In addition, the ring-shaped groove 85 is formed in the end face 241a of the mechanical connection convex portion 241, and the inside of the groove 83 is used as the electrical connection portion 244. That is, the groove 83 is termed between the electrical connection portion 244 and the sealing portion 251. For this reason, the electrical connection portion 244 is also easily squashed. In addition, contact resistance of the electrical connection portion 244 is reduced, and thus adhesion of the sealing portion 251 to the lower case 221 is not damaged.

Meanwhile, the groove 83 may not be in a ring shape formed, and may be formed intermittently along she circumferential direction on the radially inner side of the sealing portion 251.

In addition, when the heartbeat measurement device 201 is mounted on the user U, each of the electrodes 6a and 6b are pressed down by the strap 8, and thus there is a low possibility of external force being applied directly. However, when external force P in the tensile direction is applied to the electrodes 6a and 6b, a load is transmitted to the connection structure 240 formed, integrally with one end of each of the electrodes 6a and 6b in the long-side direction.

At this time, a load toward the radial outside acts on the lower case 221 through the fixing pin 78 connecting the mechanical connection convex portion 241 of the connection structure 240 to the lower case 221. Further, the mechanical connection convex portion 241 is received in the first receiving concave portion 232 formed in the lower case 221. Therefore, when the external force P in the tensile direction is applied to the electrodes 6a and 6b, an end face 241b of the mechanical connection convex portion 241 on the electrodes 6a and 6b side presses an inside surface 232a of the first receiving concave portion 232. Thereby, the lower case 221 receives the external force P acting on the electrodes 6a and 6b.

On the other hand, since the electrical connection portion 244 for electrically connecting the detection circuit board 27 to the electrodes 6a and 6b is located further at the front side than the fixing pin 78, a load due to the external force P is not easily transmitted. That is, since the electrical connection portion 244 is disposed at a position displaced in the direction perpendicular to the direction of a load of the external force P acting on the fixing pin 78 with respect to the fixing pin 78, a load due to the external force P is not easily transmitted. For this reason, even when the external force P is applied to the electrodes 6a and 6b, it is possible to stabilise the state of the connection between the electrical connection portion 244 and the conductive pin 260.

Therefore, according to the above-mentioned second embodiment, it is possible to accomplish the same effect as that of the above-mentioned first embodiment. That is, the main body portion 202 and the heartbeat detection portion 203 are formed integrally with each other, and the main body portion 202 and the heartbeat detection portion 203 are formed detachably to the fixing band 4, thereby allowing good maintenance of the heartbeat measurement device 201 to be secured.

In addition, the sealing portion 251 is provided in the periphery of the electrical connection portion 244, so that it is possible to reliably prevent sweat from the human body or foreign substances from infiltrating from the outside to the electrical connection portion 244, and to prevent the defective connection between the electrical connection portion 244 and the conductive pin 260 from occurring.

Further, even when the external force P is applied to the electrodes 6a and 6b, the state of the connection between the electrical connection portion 244 and the conductive pin 260 can be stabilised, and thus it is possible to stabilize detection accuracy of the heartbeat measurement device 201, and to provide products having high reliability.

Meanwhile, in the above-mentioned second embodiment, a case has been described in which the shape of the sealing portion 251 is formed in substantially a triangular shape in cross-section, and in a substantially circular-ring shape when seen in plan view. However, without, being limited thereto, the sealing portion may protrude from the end face 241a of the mechanical connection convex portion 241, and may be formed so as to surround the periphery of the electrical connection portion 244. For example, the sealing portion may be formed in a substantially semicircular shape in cross-section, and in a substantially rectangular shape when seen in plan view.

In addition, in the above-mentioned second embodiment, a case has been described in which the sealing portion 251 is formed integrally with the mechanical connection convex portion 241. However, without being limited thereto, the mechanical connection convex portion 241 and the sealing portion 251 may be formed separately.

Further, instead of providing the sealing portion 251 in the mechanical connection convex portion 241, the sealing portion may be protrusively provided in an area corresponding to the periphery of the electrical connection portion 244 in the bottom of the first receiving concave portion 232 of the lower case 221. In this case, the end face 241a of the mechanical connection convex portion 241 is pressed by the sealing portion of the lower case 221, and thus it is possible to secure sealing of the electrical connection portion 244 by squashing the mechanical connection convex portion 241.

In the above-mentioned second embodiment, a case has been described in which the conductive pin 260 is used in order to electrically connect the detection circuit board 27 to the electrical connection portion 244. However, the pin may be a conductive member without being limited thereto. For example, it is also possible to use a coil spring or the like instead of the conductive pin 260.

In addition, in the above-mentioned second embodiment, a case has been described in which the ring-shaped groove 83 is formed on the end face 241a of the mechanical connection convex portion 241, and the inside of the groove 83 is used as the electrical connection portion 244. Such a configuration can also be applied to the electrical connection portion 44 of the above-mentioned first embodiment. That is, a ring-shaped groove may be formed on the end face 42a of the electrical connection circular plate 42, and the inside of the groove may be used as she electrical connection portion 44.

Further, in the above-mentioned second embodiment, although a state in which any packing is not mounted to the conductive pin 260 has been described, as in the first modified example of the first embodiment, a packing may be mounted to she conductive pin 260, and sealing between the conductive pin 260 and the through hole 229 may be secured.

In addition, the present invention is not limited to the above-mentioned embodiments, and various changes may be added to the above-mentioned embodiments without departing from the scope of the present invention.

For example, in the above-mentioned embed meets, a case has been described in which the main body portions 2 and 202 and the heartbeat detection portions 3 and 203 are formed integrally with each other in the heartbeat measurement devices 1 and 201 that measure a heart rate of the user U as a biological information detection device, and the sealing portions 51 and 251 are provided in the periphery of the electrical connection portions 44 and 244 for electrically connecting the main body portions 2 and 202 and the heartbeat detection portions 3 and 203. However, such a configuration is not only applied to the heartbeat measurement devices 1 and 201, but also can be applied to various biological information detection devices. For example, as the biological information detection devices, the configuration of the above-mentioned embodiments and the modified examples can be applied to devices that measure blood pressure, body temperature, myogenic potential and the like.

In addition, in the above-mentioned embodiment, a case has been described in which the heartbeat measurement devices 1 and 201 wirelessly communicate a detected electrocardiac signal. However, without being limited thereto, wire communication may be used therefor, and simple substance measurement may be performed, for example, by providing an LCD display portion to the heartbeat measurement devices 1 and 201.

Further, in the above-mentioned embodiment, a case has been described in which in order to mount the heartbeat measurement devices 1 and 201 to the chest of the user U, the fixing band 4 is provided, and the fixing band 4 and the main body portions 2, 2', and 202 are formed detachably with each other through the strap attaching end detaching member 12 and the connection member 22. However, without being limited thereto, the fixing band 4 and the main body portions 2, 2', and 202 may be detachable with each other, and configurations other than the strap attaching and detaching member 12 and the connection member 22 may be used. For example, a pair of support walls 23 and 23 and the shaft 24 constituting the connection member 22 may be integrally formed in the lower cases 21, 21', and 221.

What is claimed is:
1. A biological information detection device comprising:
a device main body:
a biological signal detection portion, formed integrally with the device main body, which has an electrode that comes into contact with a biological surface;
a fixing portion, detachably provided to the device main body, which mounts the device main body and the biological signal detection portion to a human body;
an electrical connection portion which electrically connects the device main body to the electrode of the biological signal detection portion; and
a sealing portion surrounding the periphery of the electrical connection portion and protruding into contact with the device main body to seal the electrical connection portion from the outside environment.

2. The biological information detection device according to claim 1, wherein the sealing portion is integrally formed in the biological signal detection portion.

3. The biological information detection device according to claim 1, wherein a ring-shaped groove is formed between the electrical connection portion and the sealing portion.

4. The biological information detection device according to claim 1, wherein the biological signal detection portion is formed from conductive elastomer, and the conductive elastomer serves as the electrode.

5. The biological information detection device according to claim 1, wherein the sealing portion has a substantially triangular shape in cross section.

6. The biological information detection device according to claim 1, wherein the sealing portion has a substantially circular-ring shape when seen in plan view.

7. The biological information detection device according to claim 1, wherein the sealing portion has a substantially semicircular shape in cross section.

8. The biological information detection device according to claim 1, wherein the sealing portion has a substantially rectangular shape when seen in plan view.

9. The biological information detection device according to claim 1, further comprising a cover that covers the sealing portion.

10. A biological information detection device, comprising:
a main body portion containing a circuit board;
a biological signal detection portion integral with the main body portion and having an electrode that comes into contact with a biological surface of a human body during use of the device;
a fixing portion attached to the main body portion for mounting the main body portion to a human body so that the electrode contacts a biological surface of the human body;
an electrical connection portion that electrically connects the circuit board to the electrode; and
a compressible sealing portion surrounding a peripheral portion of the electrical connection portion and compressed between the main body portion and the electrical connection portion to seal the electrical connection portion from the outside environment.

11. The biological information detection device according to claim 10; wherein the sealing portion protrudes from the electrical connection portion toward the main body portion.

12. The biological information detection device according to claim 11; wherein the sealing portion is formed integrally with the electrical connection portion from conductive elastomer.

13. The biological information detection device according to claim 10; wherein the electrical connection portion comprises an electrical connection plate electrically connected to the electrode, and a conductive member extending through a hole in the main body portion and electrically connecting the electrical connection plate to the circuit board.

14. The biological information detection device according to claim 13; wherein the conductive member comprises a coil spring.

15. The biological information detection device according to claim 13; wherein the sealing portion surrounds the conductive member in a region where the conductive member contacts the electrical connection plate.

16. The biological information detection device according to claim 10; wherein the sealing portion protrudes from the main body portion toward the electrical connection portion.

17. The biological information detection device according to claim 10, further comprising a cover that covers the sealing portion.

18. The biological information detection device according to claim 10; wherein the sealing portion has a generally triangular cross-sectional shape.

19. The biological information detection device according to claim 10; wherein the sealing portion has a closed ring shape.

20. The biological information detection device according to claim 10; wherein the sealing portion has a generally semicircular cross-sectional shape.

* * * * *